US011638770B2

(12) United States Patent
Kolakowski (10) Patent No.: US 11,638,770 B2
(45) Date of Patent: May 2, 2023

(54) ULTRAVIOLET SANITIZING APPARATUS (71) Applicant: Boguslaw Kolakowski, Maspeth, NY (US)

(72) Inventor: Boguslaw Kolakowski, Maspeth, NY (US)

( * ) Notice: Subject to any disclaimer, the term of this patent is extended or adjusted under 35 U.S.C. 154(b) by 232 days.

(21) Appl. No.: 17/115,862

(22) Filed: Dec. 9, 2020

(65) Prior Publication Data
US 2022/0175997 A1   Jun. 9, 2022

(51) Int. Cl.
A61L 2/24 (2006.01)
A61L 2/26 (2006.01)
A61L 2/10 (2006.01)

(52) U.S. Cl.
CPC .............. A61L 2/26 (2013.01); A61L 2/10 (2013.01); A61L 2/24 (2013.01); A61L 2202/11 (2013.01)

(58) Field of Classification Search
CPC ..... A61L 2/26; A61L 2/10; A61L 2/24; A61L 2202/11
See application file for complete search history.

(56) References Cited

U.S. PATENT DOCUMENTS

| | | | | |
|---|---|---|---|---|
| 4,670,010 A | * | 6/1987 | Dragone | A61M 11/00 604/289 |
| 4,942,631 A | * | 7/1990 | Rosa | E03C 1/057 4/623 |
| 5,186,360 A | * | 2/1993 | Mease | A47K 5/122 222/63 |
| 5,522,411 A | * | 6/1996 | Johnson | A47K 10/48 134/107 |
| 6,254,625 B1 | | 7/2001 | Rosenthal | |
| 6,431,189 B1 | * | 8/2002 | Deibert | A61L 2/24 604/289 |
| 6,706,243 B1 | * | 3/2004 | Sias | A61L 2/14 604/289 |
| 7,118,589 B2 | * | 10/2006 | Vlahos | A61N 5/0614 607/94 |
| 7,989,779 B1 | * | 8/2011 | Ray | A61L 2/10 250/493.1 |
| 8,696,161 B2 | * | 4/2014 | Pan | F26B 19/00 362/249.02 |
| 8,999,261 B2 | * | 4/2015 | Benedetto | A61L 2/035 422/305 |
| 9,439,988 B2 | * | 9/2016 | Troner | A61L 2/06 |
| 9,517,284 B1 | * | 12/2016 | Stibich | A61L 2/10 |
| 9,615,884 B2 | * | 4/2017 | Armour | A61B 90/06 |

(Continued)

FOREIGN PATENT DOCUMENTS

GB   2428382   7/2005
WO   WO2007051141   5/2007

Primary Examiner — Sean M Luck (57) ABSTRACT

An ultraviolet sanitizing apparatus for elimination of germs, viruses, and bacteria includes a housing having a receiving cavity extending from a housing front side through a housing back side. A plurality of LED ultraviolet lights is coupled to the housing within the receiving cavity on each of a cavity bottom side, a cavity top side, a cavity left side, and a cavity right side. A power source is coupled to the housing and is in operational communication with the plurality of LED ultraviolet lights. A motion sensor is coupled to the housing. The motion sensor is coupled within the receiving cavity and is in operational communication with the power source to activate the LED ultraviolet lights when triggered.

12 Claims, 6 Drawing Sheets (56) References Cited

U.S. PATENT DOCUMENTS

| | | | | |
|---|---|---|---|---|
| 9,649,398 B1* | 5/2017 | York | .................. | E05B 1/0069 |
| 9,744,255 B2* | 8/2017 | Stibich | .................. | A61L 2/24 |
| 9,756,989 B2* | 9/2017 | Ophardt | .................. | H02J 7/0013 |
| 9,761,079 B1* | 9/2017 | Lin | .................. | G07F 13/025 |
| 10,335,508 B2* | 7/2019 | Cosman | .................. | F26B 3/04 |
| 2006/0041197 A1* | 2/2006 | Ophardt | .................. | G07F 9/02 |
| | | | | 600/437 |
| 2006/0171843 A1* | 8/2006 | Spears | .................. | A61L 2/24 |
| | | | | 422/292 |
| 2006/0186358 A1* | 8/2006 | Couvillion | .................. | A61L 2/10 |
| | | | | 250/504 R |
| 2007/0222554 A1* | 9/2007 | Hart | .................. | G07C 9/25 |
| | | | | 340/5.6 |
| 2007/0255266 A1 | 11/2007 | Cumbie | | |
| 2008/0199354 A1 | 8/2008 | Gordon | | |
| 2009/0299787 A1* | 12/2009 | Barnhill | .................. | G08B 21/245 |
| | | | | 434/365 |
| 2009/0314308 A1* | 12/2009 | Kim | .................. | A61L 2/0088 |
| | | | | 134/1 |
| 2010/0252569 A1* | 10/2010 | Pelfrey | .................. | A47K 5/12 |
| | | | | 136/246 |
| 2010/0266446 A1 | 10/2010 | Constantacos | | |
| 2010/0293805 A1* | 11/2010 | Chang | .................. | A45D 29/00 |
| | | | | 34/202 |
| 2011/0303694 A1* | 12/2011 | Pie | .................. | B05B 7/0018 |
| | | | | 222/137 |
| 2012/0085780 A1* | 4/2012 | Landauer | .................. | A47K 5/12 |
| | | | | 222/105 |
| 2012/0153783 A1* | 6/2012 | Shoenfeld | .................. | A61L 2/10 |
| | | | | 362/133 |
| 2012/0305804 A1* | 12/2012 | Goldman | .................. | E05B 1/0069 |
| | | | | 250/492.1 |
| 2013/0187779 A1* | 7/2013 | Pokrajac | .................. | G16H 40/20 |
| | | | | 340/573.1 |
| 2013/0256560 A1* | 10/2013 | Yerby | .................. | A61L 2/24 |
| | | | | 250/455.11 |
| 2014/0172523 A1* | 6/2014 | Stob | .................. | A47K 5/1217 |
| | | | | 222/25 |
| 2014/0252247 A1* | 9/2014 | Moskowitz | .................. | A61L 2/10 |
| | | | | 250/492.1 |
| 2016/0000951 A1* | 1/2016 | Kreiner | .................. | A61L 2/0047 |
| | | | | 250/492.1 |
| 2016/0030766 A1 | 2/2016 | Scritchfield | | |
| 2016/0158395 A1* | 6/2016 | Hughes | .................. | A61L 2/10 |
| | | | | 250/455.11 |
| 2016/0367712 A1* | 12/2016 | Robert | .................. | A61L 9/22 |
| 2017/0006993 A1* | 1/2017 | Rivero | .................. | A45D 29/00 |
| 2017/0165387 A1* | 6/2017 | Robert | .................. | A61L 9/22 |
| 2017/0246332 A1* | 8/2017 | Marshall | .................. | A61L 2/10 |
| 2018/0117191 A1* | 5/2018 | Shell | .................. | B65B 55/02 |
| 2018/0221520 A1* | 8/2018 | Nguyen | .................. | A61L 2/24 |
| 2018/0280554 A1* | 10/2018 | Khajavi | .................. | A61L 2/10 |
| 2018/0321153 A1* | 11/2018 | Llamido | .................. | G01N 21/6447 |
| 2018/0357886 A1* | 12/2018 | Tavori | .................. | G16H 40/20 |
| 2019/0117802 A1 | 4/2019 | Hishinuma | | |
| 2019/0192705 A1* | 6/2019 | Masyk | .................. | A61L 2/10 |
| 2019/0321499 A1* | 10/2019 | Igarashi | .................. | A61L 2/0047 |
| 2020/0261608 A1* | 8/2020 | Crosby | .................. | A61L 2/10 |

\* cited by examiner

ULTRAVIOLET SANITIZING APPARATUS

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to sanitizing devices and more particularly pertains to a new sanitizing device for elimination of germs, viruses, and bacteria.

(2) Description of Related Art Including Information Disclosed Under 37 CFR 1.97 and 1.98

The prior art relates to sanitizing devices. Known devices utilize ultraviolet lighting for disinfecting purposes, yet largely fail to provide 360° of light exposure. These devices also lack motion sensor activation. Known devices also often do not accommodate items such as doorknobs and money.

BRIEF SUMMARY OF THE INVENTION

An embodiment of the disclosure meets the needs presented above by generally comprising a housing having a housing front side, a housing back side, a housing top side, a housing bottom side, a housing left side, and a housing right side. The housing front side has a receiving cavity extending through the housing back side. A plurality of light emitting diode (LED) ultraviolet lights is coupled to the housing within the receiving cavity on each of a cavity bottom side, a cavity top side, a cavity left side, and a cavity right side. A power source is coupled to the housing and is in operational communication with the plurality of LED ultraviolet lights. A motion sensor is coupled to the housing. The motion sensor is coupled within the receiving cavity and is in operational communication with the power source to activate the LED ultraviolet lights when triggered.

An alternative embodiment of the disclosure generally comprises a door having a door knob. A housing has a housing front side, a housing back side, a housing top side, a housing bottom side, a housing left side, and a housing right side. The housing front side has a receiving cavity extending through the housing back side. The housing back side is coupled to the door with the receiving cavity surrounding the door knob. A plurality of LED ultraviolet lights is coupled to the housing within the receiving cavity on each of a cavity bottom side, a cavity top side, a cavity left side, and a cavity right side. A power source is coupled to the housing and is in operational communication with the plurality of LED ultraviolet lights. A motion sensor is coupled to the housing. The motion sensor is coupled within the receiving cavity and is in operational communication with the power source to activate the LED ultraviolet lights when triggered.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

With reference now to the drawings, and in particular to FIGS. 1 through 6 thereof, a new sanitizing device embodying the principles and concepts of an embodiment of the disclosure and generally designated by the reference numeral 10 will be described.

Figure 1:
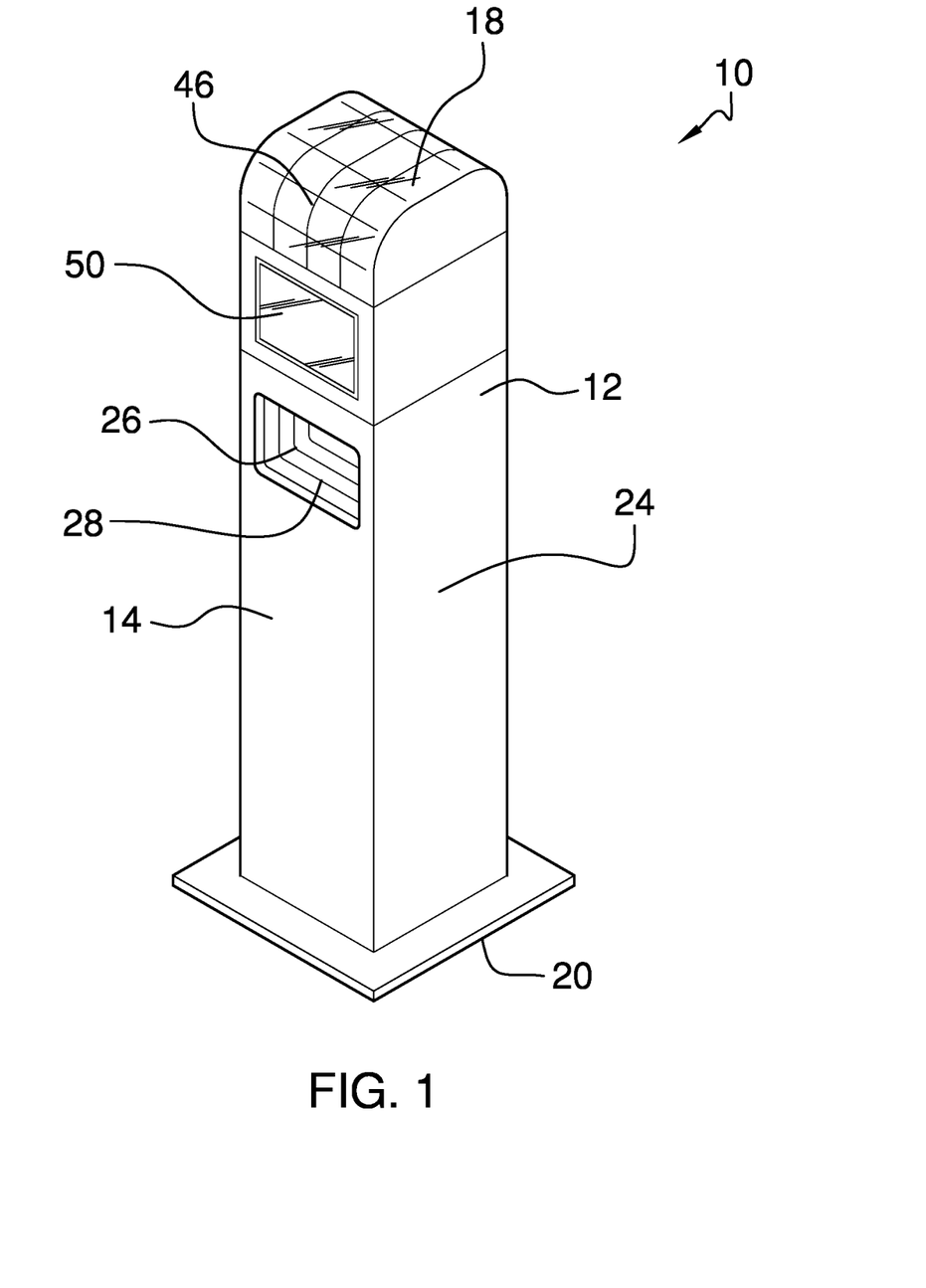
FIG. 1 is an isometric view of an ultraviolet sanitizing apparatus according to an embodiment of the disclosure.
Figure 2:
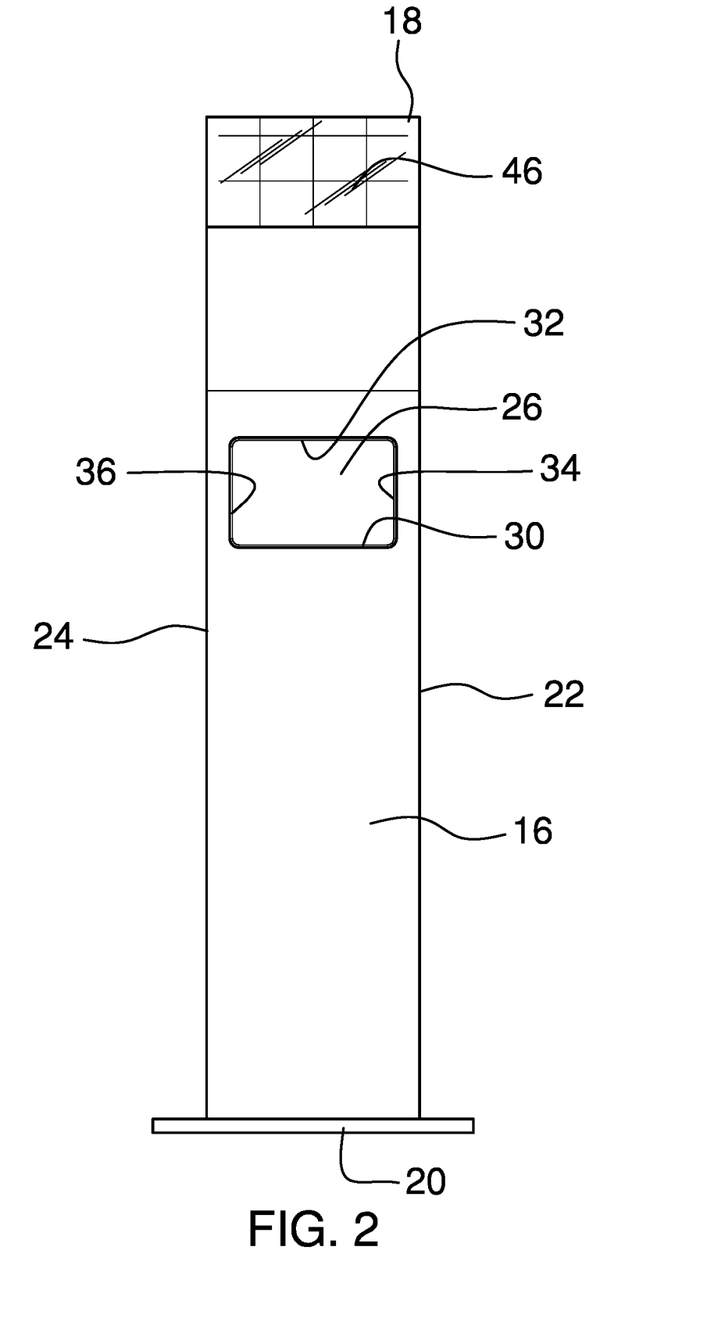
FIG. 2 is a rear elevation view of an embodiment of the disclosure.
Figure 3:
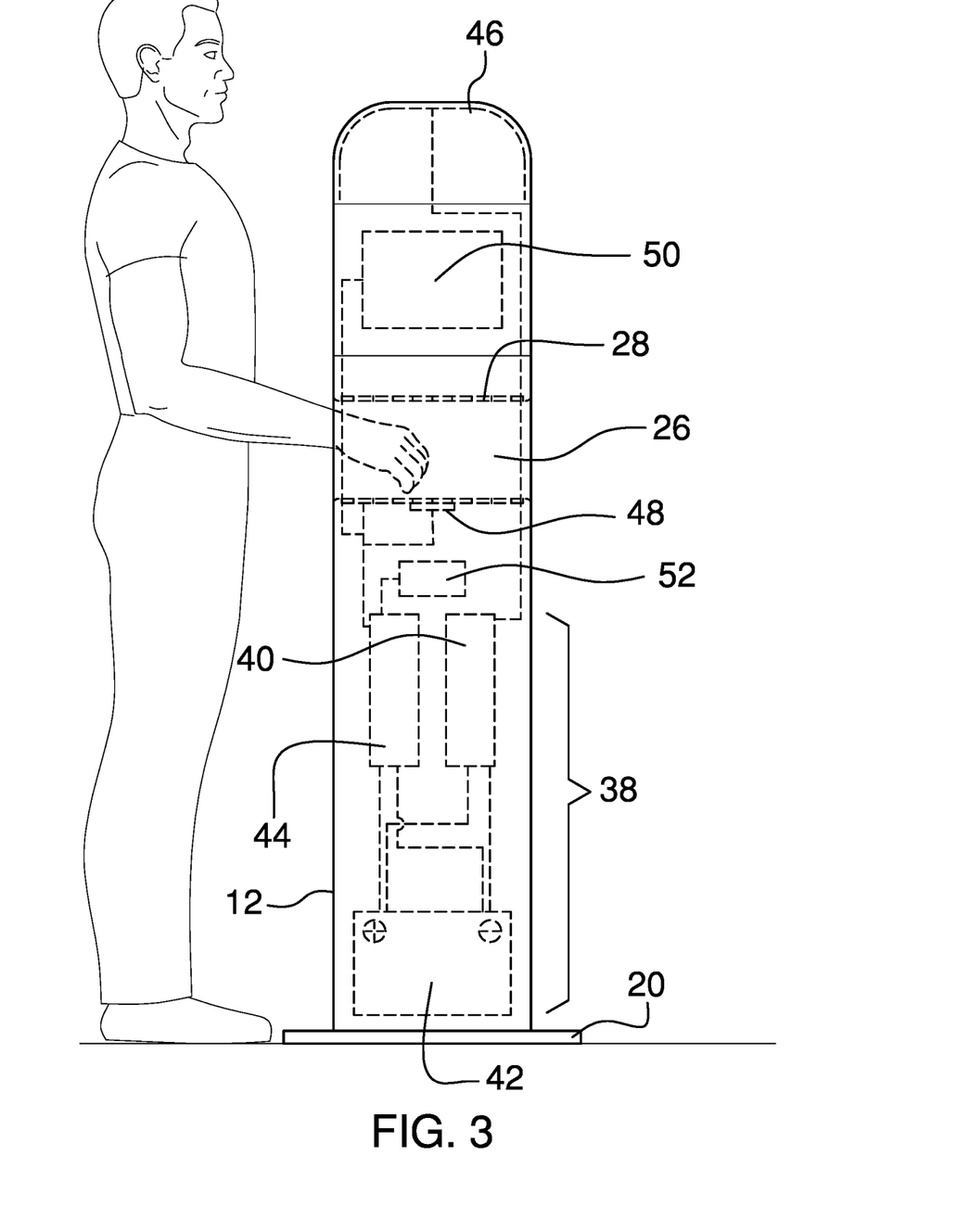
FIG. 3 is a side elevation view of an embodiment of the disclosure.

As best illustrated in FIGS. 1 through 6, the ultraviolet sanitizing apparatus 10 generally comprises a housing 12 having a housing front side 14, a housing back side 16, a housing top side 18, a housing bottom side 20, a housing left side 22, and a housing right side 24. The housing front side 14 has a receiving cavity 26 extending through the housing back side 16. The housing 12 may be free-standing with the housing bottom side 20 extending outwards to stabilize the housing 12 as seen in FIGS. 1-3. The housing top side 18 may have rounded edges meeting the housing front side 14 and the housing back side 16.

A plurality of LED ultraviolet lights 28 is coupled to the housing 12. The plurality of LED ultraviolet lights 28 is coupled within the receiving cavity 26 on each of a cavity bottom side 30, a cavity top side 32, a cavity left side 34, and a cavity right side 36. The plurality of LED ultraviolet lights 28 kill germs, bacteria, and viruses when activated. Each LED ultraviolet light 28 has an immediate on cycle and operates within a power range that is not harmful to human skin.

A power source 38 is coupled to the housing 12. The power source 38 may be in operational communication with the plurality of LED ultraviolet lights 28. The power source 38 may include a charger 40, a battery 42, and a transformer 44. A solar panel 46 may be coupled to the housing 12 and in operational communication with the charger 40 to charge the battery 42. The solar panel 46 may be coupled to the housing top side 18 and may extend onto the housing front side 14 and the housing back side 16.

A motion sensor 48 is coupled to the housing 12. The motion sensor 48 is coupled within the receiving cavity 26 and is in operational communication with the power source 38 to activate the plurality of LED ultraviolet lights 28 when triggered. The plurality of LED ultraviolet lights 28 may be activated for a programmed time interval or may be manipulated by a touch screen control panel 50 coupled to the housing 12. The touch screen control panel 50 is coupled to the housing front side 14 and is in operational communication with the motion sensor 48.

A Wi-Fi transceiver 52 may be coupled within the housing 12. The Wi-Fi transceiver 52 is in operational communication with the power source 38, the motion sensor 48, and the control panel 50 in order to detect any malfunction and notify a service technician via the internet.

Figure 4:
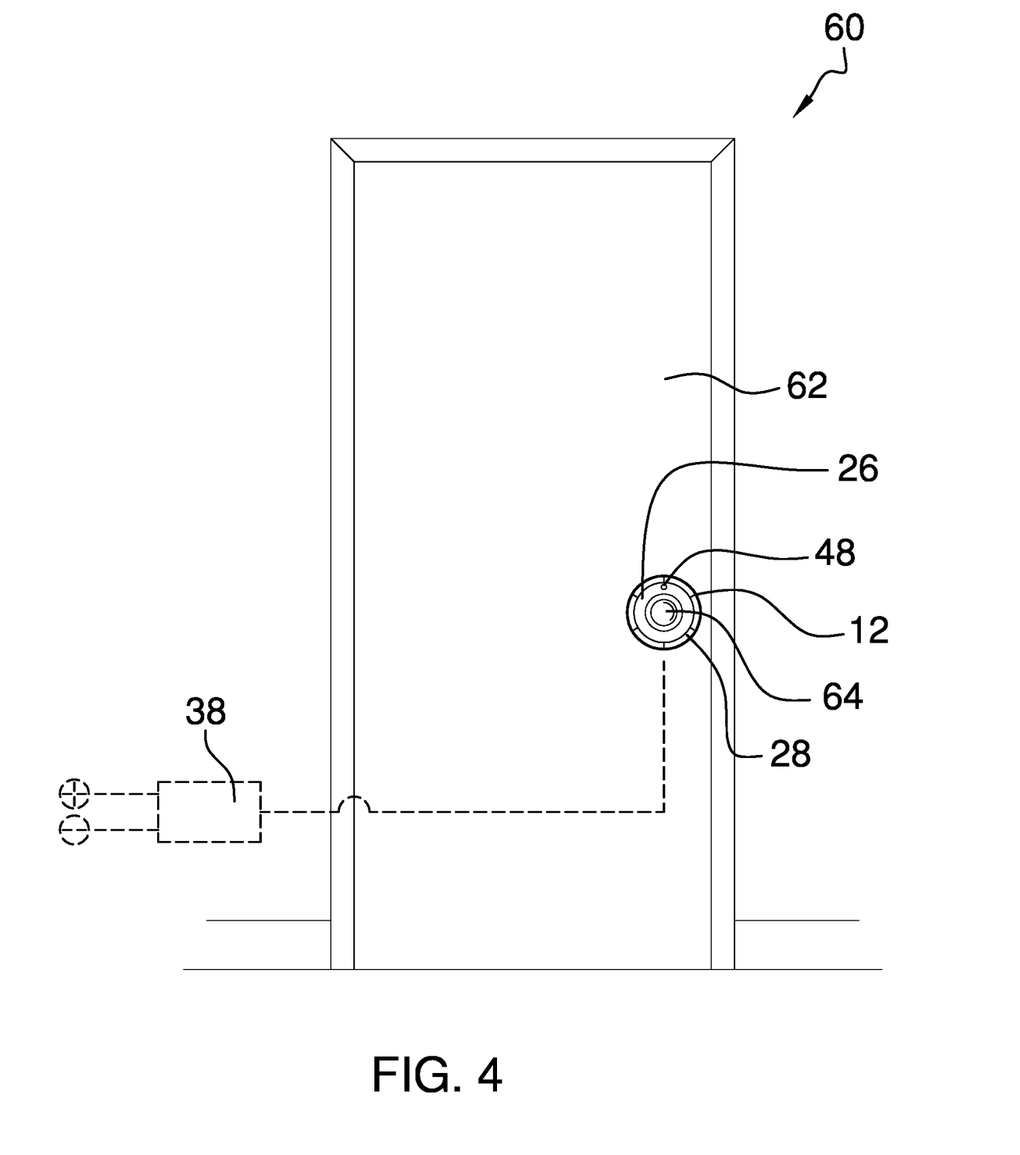
FIG. 4 is a front elevation view of an embodiment of the disclosure.
Figure 5:
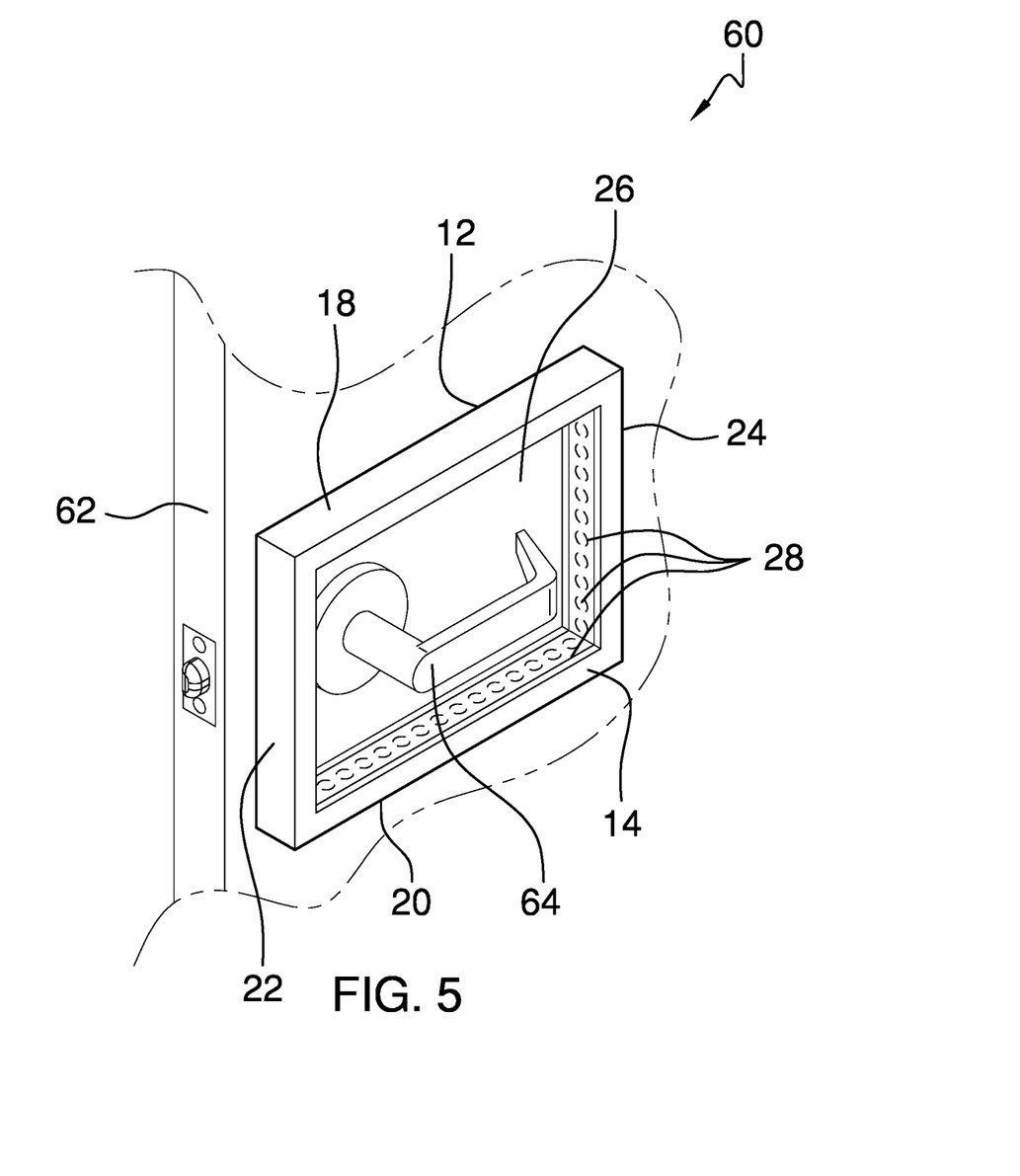
FIG. 5 is an isometric view of an embodiment of the disclosure.

A first alternative embodiment of the invention 60 includes a door 62 having a door knob 64. The housing back side 16 is coupled to the door 60 with the receiving cavity 26 surrounding the door knob 64. The housing front side 14 may be circular as shown in FIG. 4 or rectangular as shown in FIG. 5.

Figure 6:
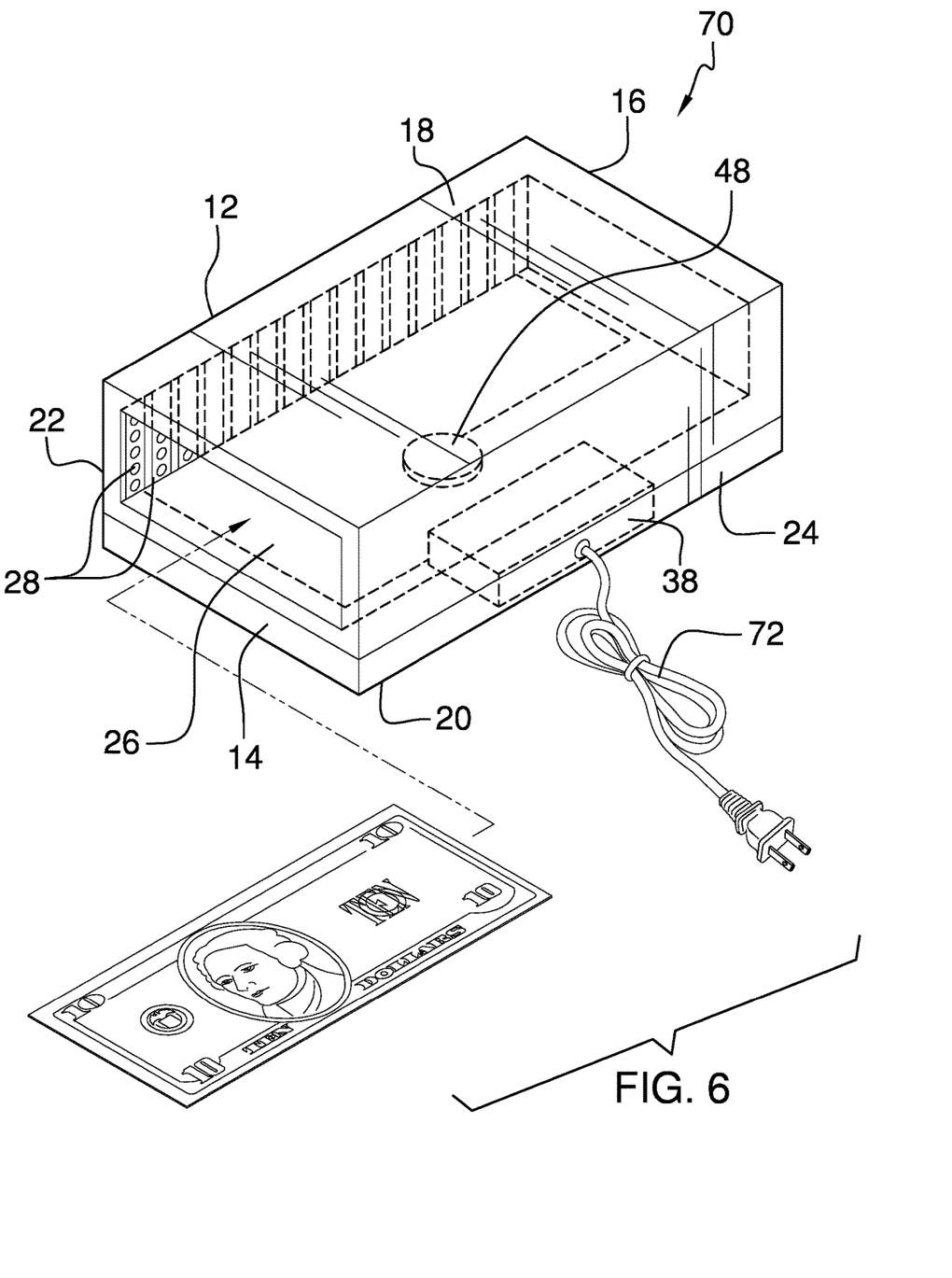
FIG. 6 is an isometric view of an embodiment of the disclosure.

In a second alternative embodiment of the invention 70, the housing 12 is configured to rest on a counter or a table and the receiving cavity 26 is dimensioned and configured to receive money as shown in FIG. 6. The power source 38 may include a standard wall plug 72.

In use, the object in need of sanitation is placed within the receiving cavity 26 to trigger the motion sensor 48 and activate the plurality of LED ultraviolet lights 28.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An ultraviolet sanitizing apparatus comprising:
   a housing having a housing front side, a housing back side, a housing top side, a housing bottom side, a housing left side, and a housing right side, the housing front side having a receiving cavity extending through the housing back side, the receiving cavity being configured for permitting passage of objects at least partially therethrough;
   a plurality of LED ultraviolet lights coupled to the housing, the plurality of LED ultraviolet lights being coupled within the receiving cavity on each of a cavity bottom side, a cavity top side, a cavity left side, and a cavity right side;
   a power source coupled to the housing, the power source being in operational communication with the plurality of LED ultraviolet lights; and
   a motion sensor coupled to the housing, the motion sensor being coupled within the receiving cavity and being in operational communication with the power source to activate the LED ultraviolet lights when triggered.

2. The ultraviolet sanitizing apparatus of claim 1 further comprising the housing being free-standing and the housing bottom side extending outwards to stabilize the housing.

3. The ultraviolet sanitizing apparatus of claim 1 further comprising a solar panel coupled to the housing, the solar panel being coupled to the housing top side and being in operational communication with the power source.

4. The ultraviolet sanitizing apparatus of claim 3 further comprising the housing top side having rounded edges meeting the housing front side and the housing back side; the solar panel extending onto the housing front side and the housing back side.

5. The ultraviolet sanitizing apparatus of claim 3 further comprising the power source including a charger, a battery, and a transformer.

6. The ultraviolet sanitizing apparatus of claim 1 further comprising a touch screen control panel coupled to the housing, the touch screen control panel being coupled to the housing front side and being in operational communication with the motion sensor.

7. The ultraviolet sanitizing apparatus of claim 6 further comprising a Wi-Fi transceiver coupled within the housing, the Wi-Fi transceiver being in operational communication with the power source, the motion sensor, and the control panel.

8. An ultraviolet sanitizing apparatus comprising:
   a housing having a housing front side, a housing back side, a housing top side, a housing bottom side, a housing left side, and a housing right side, the housing front side having a receiving cavity extending through the housing back side, the receiving cavity being configured for permitting passage of objects at least partially therethrough, the receiving cavity having a size being configured to receive an arm of a user at least partially therethrough, the housing being free-standing and the housing bottom side extending outwards to stabilize the housing, the housing top side having rounded edges meeting the housing front side and the housing back side;
   a plurality of LED ultraviolet lights coupled to the housing, the plurality of LED ultraviolet lights being coupled within the receiving cavity on each of a cavity bottom side, a cavity top side, a cavity left side, and a cavity right side;

a power source coupled to the housing, the power source being in operational communication with the plurality of LED ultraviolet lights, the power source including a charger, a battery, and a transformer;

a solar panel coupled to the housing, the solar panel being coupled to the housing top side and extending onto the housing front side and the housing back side, the solar panel being in operational communication with the power source;

a motion sensor coupled to the housing, the motion sensor being coupled within the receiving cavity and being in operational communication with the power source to activate the LED ultraviolet lights when triggered;

a touch screen control panel coupled to the housing, the touch screen control panel being coupled to the housing front side and being in operational communication with the motion sensor; and a Wi-Fi transceiver coupled within the housing, the Wi-Fi transceiver being in operational communication with the power source, the motion sensor, and the control panel.

9. An ultraviolet sanitizing apparatus and door combination comprising:

a door, the door having a door knob;

a housing having a housing front side, a housing back side, a housing top side, a housing bottom side, a housing left side, and a housing right side, the housing front side having a receiving cavity extending through the housing back side, the housing back side being coupled to the door with the receiving cavity surrounding the door knob;

a plurality of LED ultraviolet lights coupled to the housing, the plurality of LED ultraviolet lights being coupled within the receiving cavity on each of a cavity bottom side, a cavity top side, a cavity left side, and a cavity right side;

a power source coupled to the housing, the power source being in operational communication with the plurality of LED ultraviolet lights; and a motion sensor coupled to the housing, the motion sensor being coupled within the receiving cavity and being in operational communication with the power source to activate the LED ultraviolet lights when triggered.

10. The ultraviolet sanitizing apparatus of claim 9 further comprising the housing front side being rectangular.

11. The ultraviolet sanitizing apparatus of claim 9 further comprising the housing front side being circular.

12. The ultraviolet sanitizing apparatus of claim 1 further comprising the housing being configured to rest on a counter or a table and the receiving cavity having a size being configured for receiving paper currency, therethrough and for preventing passage of an arm of a user therethrough.

* * * * *